United States Patent [19]

Dawson et al.

[11] Patent Number: 4,625,563
[45] Date of Patent: Dec. 2, 1986

[54] PORTABLE BEND TESTER

[76] Inventors: Richard S. Dawson; Daniel S. Dawson, both of 1717 Solano Way, Bldg. 20, Concord, Calif. 94520

[21] Appl. No.: 792,027

[22] Filed: Oct. 28, 1985

[51] Int. Cl.[4] .............................................. G01N 3/20
[52] U.S. Cl. .................................................... 73/850
[58] Field of Search ................. 73/849, 850, 851, 852, 73/853, 854, 856, 859

[56] References Cited

U.S. PATENT DOCUMENTS

| | | | |
|---|---|---|---|
| 1,200,086 | 10/1916 | Cruser | 73/851 |
| 1,924,866 | 8/1933 | Lewis | 73/851 |
| 2,748,829 | 6/1955 | Korenak | 73/852 |
| 3,500,679 | 3/1970 | Smith | 73/850 |
| 3,906,784 | 9/1975 | Coulstring | 73/850 |
| 4,573,360 | 3/1986 | Yoneda | 73/850 |

FOREIGN PATENT DOCUMENTS

| | | | |
|---|---|---|---|
| 920942 | 11/1954 | Fed. Rep. of Germany | 73/850 |
| 0805113 | 2/1981 | U.S.S.R. | 73/850 |
| 1155904 | 5/1985 | U.S.S.R. | 73/850 |

Primary Examiner—Stewart J. Levy
Assistant Examiner—Robert R. Raevis

[57] ABSTRACT

This bend tester is lightweight and portable for on the site use to qualify welders. Primarily, it consists of a frame on a base, and a platform with a yoke on it is elevatable in the frame to bend metal by a plunger mounted to a top plate of said frame.

2 Claims, 5 Drawing Figures

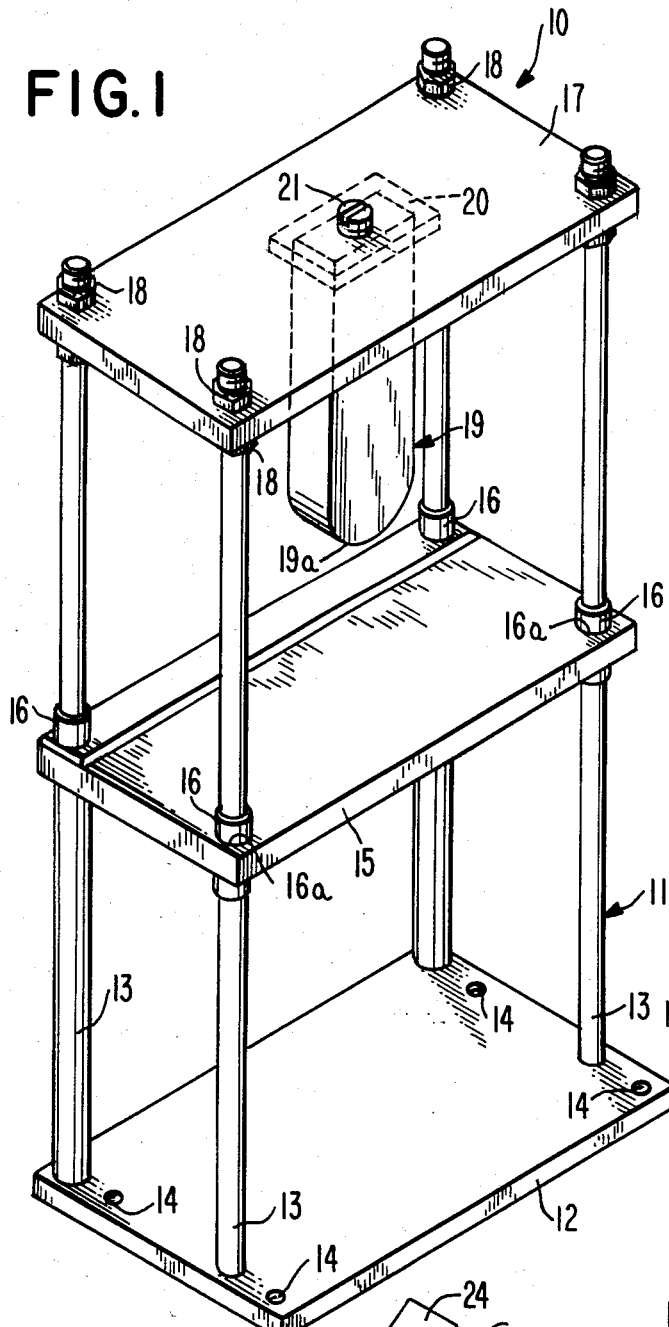
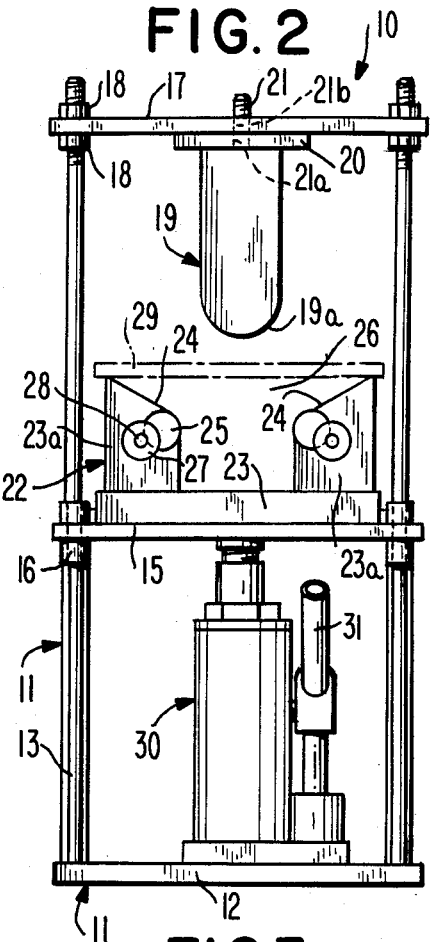
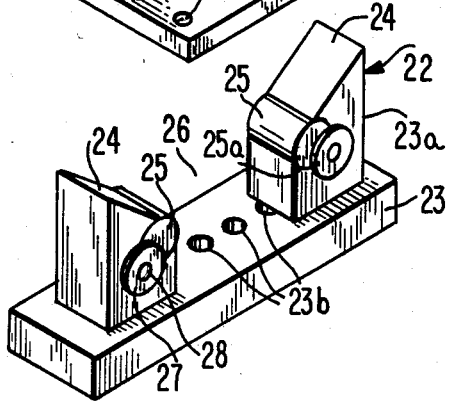
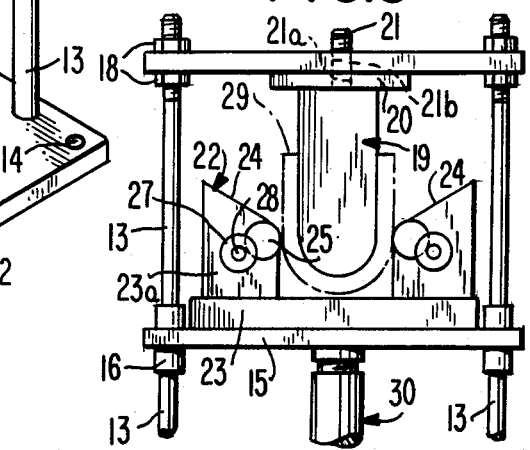
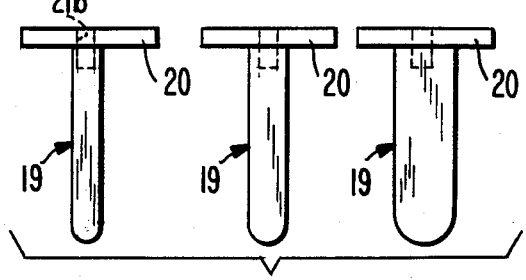

PORTABLE BEND TESTER

BACKGROUND OF THE INVENTION

1. Field of the Invention

This invention relates to metal testing devices, and, more particularly, to a portable bend tester.

2. Description of Prior Art

Bend testers have been devised to qualify welders, but are not portable. The tester, in accordance with the present invention, is portable and weighs approximately one hundred pounds, thus making it easy to qualify welders right on the job site.

The principal object of this invention is to provide a portable bend tester, which will be used to qualify welders on a job site.

Another object of this invention is to provide a portable bend tester, which will be unique, in that it will be light in weight, adjustable, and will bend metal one-eighth of an inch thick, one-fourth of an inch thick, three-eighths of an inch thick, and one-half of an inch thick.

A further object of this invention is to provide a bend tester, which will be only two feet high and one foot square, making it easy to carry and store, and by employing the same principles in fabricating, may be made to bend even thicker metal.

BRIEF DESCRIPTION OF THE DRAWINGS

FIG. 1 is a fragmentary perspective view of the present invention;

FIG. 2 is a front elevational view of the invention, showing a metal pipe in phantom;

FIG. 3 is a fragmentary view of FIG. 2, showing the pipe completely bent;

FIG. 4 is an enlarged perspective view of the yoke, shown removed from the invention, and FIG. 5 is a vertical front elevational view of optional plungers for the invention.

SUMMARY OF THE INVENTION

A portable bend tester which is used to qualify welders, comprising a press or cage having an adjustable yoke for bending metal at a weld to determine if the weld is made properly. The press or cage includes a platform which is elevatable by means of a jack, and a yoke is employed on the platform for the placement of the metal to be bent by a plunger received in the top of the press or cage.

DETAILED DESCRIPTION

Accordingly, a tester 10 is shown to include a frame 11 having a base 12. Four rods 13 are provided and externally threaded on their ends and received in threaded openings 14 through base 12. A platform 15 is provided and includes sleeves 16, which are suitably fixedly secured in openings 16a thereof, and rods 13 are slideably received in sleeves 16, for a purpose which will hereinafter be described. A top plate 17 is provided and includes an opening through each corner, not shown, which receives the upper ends of the rods 13, and the ends of rods 13 receive nut fasteners 18, below and above plate 17 for securing plate 17 in elevated position. A plunger 19 is provided and has a rounded end 19a for bend-forming metal, and a mounting base 20 is suitably fixedly secured to the opposite end of plunger 19. A threaded stud 21 is threaded into a threaded opening 21a in base 20 and is received in opening 21b of top plate 17. A yoke 22 is provided and includes a base 23 having vertical posts 23a. The top surfaces 24 of posts 23a, are at thirty degrees of angle to take the pressure off of the rollers 25 which are received in the cutout openings 25a of posts 23a, and a plurality of spaced openings 23b are provided through base 23 for receiving the mounting pins, not shown, of posts 23a. The openings 23b enable the space 26 between posts 23a to be closed or opened to any desired distance, and the rollers are held in place by side discs 27 and fasteners 28. A pipe 29 that is to be bent, is placed on the top of the posts 23a and a jack 30 with a handle 31 is positioned on the base 12 below the platform 15, to elevate platform 15 to bend-form the pipe 29.

It shall be noted, that tester 10 is designed to bend six to twelve-inch long strips of metal, three-fourths to one and one-fourth of an inch wide, one hundred eighty degrees, to determine the strength of the metal, and if the metal is defective, it will crack at the weld. However, the primary purpose of tester 10 is to qualify welders.

In use, platform 15 is lifted and the jack 30 is placed beneath the platform 15 where it will rest. A welder will weld two pieces of pipe 29 together end to end, and the pipe 29 is then cut longitudinally into strips and ground flush, after which, the pipe 29 is placed on the top of the yoke 22. The handle 31 of the jack 30 is then used to operate jack 30 to elevate the platform and the yoke 22 with the pipe thereon. The plunger 19 then urges the pipe 29 downward between the posts 23a of yoke 22, thus forming the pipe 29 in a "U"-shape between the rollers 25. If the weld in the pipe 29 cracks, the welder is disqualified.

Looking now at FIG. 5, plungers 19 are shown of different sizes, and it is to be recognized, that jack 30 may be any twelve-ton type that is nine and one-fourth inches in height or less, and the plungers 19 are designed to bend metal thicknesses of one-eighth, one-fourth, three-eighths, and one-half inch when the yoke is adjusted properly.

While various changes may be made in the detail construction, it is understood that such changes will be within the spirit and scope of the present invention, as is defined by the appended claims.

What we now claim is:

1. A portable bend tester, comprising, in combination, a frame including a horizontal base at a lower end thereof, a plurality of upwardly vertical rods fixedly mounted on said base, a horizontal platform vertically slidable along a longitudinally intermediate portion of said rods, and a horizontal top plate affixed upon an upper end of said rods; and an upright jack mounted upon said base bearing against an underside of said platform, a downwardly plunger mounted on an underside of said top plate, a lower end of said plunger being rounded, and a yoke being mounted upon an upper side of said platform; said yoke comprising a base block, a pair of spaced apart, upwardly extending posts mounted upon said base block, a top surface of each said post being at an inclined angle, said inclined surfaces of both said pair of posts being positioned to incline downwardly toward a common space formed between said posts, each said post having a vertical side surface adjacent said space, and a roller seated at a junctioning corner of said inclined top surface and said vertical side surface, said roller being rotatable about a horizontal axis and resting against a surface of a rounded fastener.

2. The combination as set forth in claim 1, wherein said posts include downwardly pins selectively received in a row of openings in said base block for adjustable spacing apart.

* * * * *